(12) United States Patent
Mitsuzawa

(10) Patent No.: US 9,193,803 B2
(45) Date of Patent: Nov. 24, 2015

(54) PRETREATED PRODUCT OF LIGNOCELLULOSIC BIOMASS FOR SACCHARIFICATION AND PROCESS FOR PRODUCING THE SAME

(71) Applicant: HONDA MOTOR CO., LTD., Tokyo (JP)

(72) Inventor: Shigenobu Mitsuzawa, Saitama (JP)

(73) Assignee: HONDA MOTOR CO., LTD., Tokyo (JP)

(*) Notice: Subject to any disclaimer, the term of this patent is extended or adjusted under 35 U.S.C. 154(b) by 0 days.

(21) Appl. No.: 13/903,708

(22) Filed: May 28, 2013

(65) Prior Publication Data

US 2014/0060521 A1    Mar. 6, 2014

(30) Foreign Application Priority Data

Aug. 28, 2012    (JP) .................. 2012-187288

(51) Int. Cl.
| | |
|---|---|
| *C08B 1/00* | (2006.01) |
| *C08H 7/00* | (2011.01) |
| *C08H 8/00* | (2010.01) |
| *C08L 97/00* | (2006.01) |
| *C08L 97/02* | (2006.01) |

(52) U.S. Cl.
CPC ........ *C08B 1/003* (2013.01); *C08H 6/00* (2013.01); *C08H 8/00* (2013.01); *C08L 97/005* (2013.01); *C08L 97/02* (2013.01); *C12P 2201/00* (2013.01)

(58) Field of Classification Search
None
See application file for complete search history.

(56) References Cited

U.S. PATENT DOCUMENTS 8,765,405 B2 *   7/2014  Kurihara et al. .............. 435/41
2011/0250645 A1  10/2011 Schiffino et al.

FOREIGN PATENT DOCUMENTS

| JP | 2010-115162 | | 5/2010 |
|---|---|---|---|
| JP | 2012-070725 A | | 4/2012 |
| WO | 2010/067785 | | 6/2010 |
| WO | WO2010/067785 | * | 6/2010 |
| WO | 2011/114914 | | 9/2011 |

OTHER PUBLICATIONS

Effect of Pore Size in Substrate and Diffusion of Enzyme on Hydrolysis of Cellulosic Materials with Cellulases Mitsuo Tanaka et al. Biotechnology and Bioengineering, vol. 32, pp. 698-706 (1988).*

(Continued)

*Primary Examiner* — Melvin C Mayes
*Assistant Examiner* — Douglas Call
(74) *Attorney, Agent, or Firm* — Rankin, Hill & Clark LLP

(57) ABSTRACT

Provided is a pretreated product for saccharification, obtained by a pretreatment alone which allows an efficient enzymatic saccharification treatment to thereby obtain a saccharified solution having a uniform quality. A pretreated product for saccharification where lignin 5 is dissociated or a substrate 1 is swollen is obtained by pretreating the substrate 1. The substrate 1 has 60 to 80% of the pores having a diameter of 10 to 50 nm. In a process for producing the pretreated product for saccharification, a substrate mixture obtained by mixing the substrate 1 and ammonia water is maintained at a predetermined temperature for a predetermined period of time to thereby separate a part of hemicellulose 4 having a molecular weight of $7.8 \times 10^3$ to $2.0 \times 10^6$.

3 Claims, 3 Drawing Sheets

(56) References Cited

OTHER PUBLICATIONS

Effect of Pretreatments and Fermentation on Pore Size in Cellulosic Materials K.W. Lin et al. Biotechnology and Bioengineering, vol. 27, pp. 1427-1433 (1985).*

Molecular properties of hemicelluloses located in the surface and inner layer of hardwood and softwood pulps Olof Dahlman et al. Cellulose vol. 10, pp. 325-334, 2003.*

Japanese Office Action dated Sep. 15, 2015, 4 pages.

Kim, et al. "Bioethanol Production from Barley Hull Using SAA (Soaking in Aqueous Ammonia) Pretreatment", Science Direct, Bioresource Technology 99 (2008) vol. 99, No. 13, p. 5694-5702, 10 pages.

Ko, et al. "Ethanol Production from Rice Straw Using Optimized Aqueous-Ammonia Soaking Pretreatment and Simultaneous Saccharification and Fermentation Processes", Bioresource Technology, (2009) vol. 100. No. 19, p. 4374-4380, 8 pages.

* cited by examiner

PRETREATED PRODUCT OF LIGNOCELLULOSIC BIOMASS FOR SACCHARIFICATION AND PROCESS FOR PRODUCING THE SAME

BACKGROUND OF THE INVENTION

Detailed Description of the Invention

1. Field of the Invention

The present invention relates to a pretreated product of lignocellulosic biomass for saccharification and a process for producing the same.

2. Description of the Related Art

It has been studied to produce bioethanol using inedible lignocellulosic biomass and mix the bioethanol with liquid hydrocarbon such as gasoline to use for the automotive fuel. The lignocellulosic biomass is converted to a saccharified solution containing saccharides such as glucose, xylose and arabinose by hydrolyzing cellulose and hemicellulose contained therein using enzymatic saccharification, and the saccharides in the obtained saccharified solution can be fermented to obtain ethanol. An example of the lignocellulosic biomass is rice straw.

However, the lignocellulose contains lignin in addition to the cellulose and hemicellulose, which are firmly bonded to the lignin, making it impossible to readily carry out the enzymatic saccharification reaction without further treatment. For this reason, when the lignocellulose as a substrate is subjected to the enzymatic saccharification reaction, it is desirable that the substrate be treated by, in advance, dissociating lignin from the substrate or swelling the substrate so that a saccharification enzyme can contact the substrate.

In the present application, the term "dissociation" means the cleavage of at least a part of the bonds between lignin and cellulose or hemicellulose. The term "swelling" means the expansion of crystalline cellulose, due to the liquid permeation, caused by the gap formed in cellulose or hemicellulose composing the crystalline cellulose or caused by the gap formed inside the cellulose fiber.

For the pretreatment described above, it is known that lignocelluosic biomass such as rice straw is treated with ammonia to prepare a pretreated product for saccharification. It is also proposed that, during this procedure, the ester bond (ferulate crosslinking) between the hemicellulose and lignin is cleaved to achieve a reside gal ratio of the ester bond of the pretreated product for saccharification of 90% or less (see, for example, Japanese Patent Laid-Open No. 2012-70725).

According to the conventional technique described above, when the residual ratio of the ester bond in the pretreated product for saccharification is 90% or less, the efficiency of enzymatic saccharification is believed to improve.

However, to improve the efficiency of enzymatic saccharification in the conventional technique, the pretreated product for saccharification must further be subjected to a wet mill, hence inconvenient.

The lignocellulosic biomass come in different qualities, in terms of biomass properties, depending on the season and region harvested, or the variety, it is hence difficult to provide the saccharified solution having a uniform quality even when subjected to the enzymatic saccharification under the same conditions, hence inconvenient.

SUMMARY OF THE INVENTION

The present invention has an object to provide a pretreated product for saccharification which overcomes the above inconveniences, can be enzymatically saccharified efficiently by a pretreatment alone and is capable of providing the saccharified solution having a uniform quality regardless of the lignocellulosic biomass quality, and a process for producing the same.

To achieve such objects, in the pretreated product of lignocellulosic biomass for saccharification of the present invention, in which lignin is dissociated from the substrate or the substrate is swelled, obtained by pretreating the lignocellulosic biomass as a substrate before saccharification, 60 to 80% of all pores of the substrate have a diameter ranging from 10 to 50 nm.

The pretreated product of lignocellulosic biomass for saccharification of the present invention has the pored substrate, and when 60 to 80% of all pores have a diameter ranging from 10 to 50 nm, a saccharification enzyme is easily absorbed into the substrate. As a result, in the pretreated product for saccharification, the saccharification enzyme can contact the cellulose and hemicellulose contained in the substrate, thereby improving the enzymatic saccharification efficiency.

According to the pretreated product for saccharification of the present invention, when 60 to 80% of all pores of the substrate have a diameter ranging from 10 to 50 nm, a saccharified solution having a uniform quality can be obtained regardless of the quality difference in the lignocellulosic biomass as a substrate.

In the pretreated product for saccharification of the present invention, when the pore has a diameter smaller than 10 nm, the saccharification enzyme cannot be absorbed into the substrate, failing to improve the enzymatic saccharification efficiency. On the other hand, when the pore has a diameter larger than 50 nm, the time required for the pretreatment becomes enormous.

When the pore having the diameter of the above range is below 60% of all substrate pores, the saccharification enzyme cannot be sufficiently absorbed into the substrate, failing to improve the enzymatic saccharification efficiency. On the other hand, when the pore having the diameter of the above range exceeds 80% of all substrate pores, the time required for the pretreatment becomes enormous.

The process for producing a pretreated product of lignocellulosic biomass for saccharification of the present invention, in which lignin is dissociated from the substrate or the substrate is swelled, obtained by pretreating the lignocellulosic biomass as a substrate before saccharification, comprises maintaining a substrate mixture obtained by mixing the substrate and ammonia water at a predetermined temperature for a predetermined period of time, separating at least a part of the hemicellulose having a molecular weight ranging from $7.8 \times 10^3$ to $2.0 \times 10^6$ among the hemicellulose composing the substrate, forming pores having a diameter ranging from 10 to 50 nm in the substrate, and adjusting the pores having the diameter of such a range to be 60 to 80% of all substrate pores.

The lignocellulosic biomass as the substrate has a structure wherein hemicellulose is positioned on the outer surface of microfibril composed of cellulose and further lignin is positioned on the outer surface of the hemicellulose. The hemicellulose is bonded to the lignin described earlier by the ferulate crosslinking.

The substrate having the above structure swells, when the substrate mixture obtained by mixing ammonia water therewith is kept at a predetermined temperature for a predetermined period of time, while the ferulate crosslinking is cleaved and lignin is separated from the substrate. At this time, at least a part of the hemicellulose composing the substrate is also separated from the substrate.

When the hemicellulose separated from the substrate has a molecular weight ranging from $7.8 \times 10^3$ to $2.0 \times 10^6$, pores having a diameter ranging from 10 to 50 nm are formed between the microfibril composed of the cellulose in the substrate and the dissociated lignin. In addition, the pores having the diameter of the above range are formed in a range from 60 to 80% of all substrate pores.

In the process for producing a pretreated product for saccharification of the present invention, when a molecular weight of the hemicellulose separated from the substrate is below $7.8 \times 10^3$, the diameter of pore formed in the substrate is smaller than 10 nm and the pore formed is below 60% of all substrate pores. On the other hand, when a molecular weight of the hemicellulose separated from the substrate exceeds $2.0 \times 10^6$, the diameter of pore formed in the substrate is larger than 50 nm and the pore formed exceeds 80% of all substrate pores, requiring enormous time for the pretreatment.

In the process for producing a pretreated product for saccharification of the present invention, the substrate mixture is preferably obtained by mixing the substrate and ammonia water in a concentration ranging from 20 to 30% by mass in a mass ratio of the substrate:ammonia water=1:0.7 to 1:4. When a concentration of the ammonia water is below 20% by mass, the effects for swelling the substrate, dissociating lignin from the substrate and separating the hemicellulose having the molecular weight of the above range may not sufficiently be attained. On the other hand, when a concentration of the ammonia water exceeds 30% by mass, the effects for swelling the substrate, dissociating lignin from the substrate and separating the hemicellulose having the molecular weight of the above range may not be expected to provide more effects than those.

When the ammonia water is below 0.7 parts by mass with respect to 1 part by mass of the substrate, the ammonia water is too little to homogeneously impregnate the substrate therewith. As a result, the effects for swelling the substrate, dissociating lignin from the substrate and separating the hemicellulose having the molecular weight of the above range may not sufficiently be attained.

On the other hand, when the ammonia water exceeds 4 parts by mass with respect to 1 part by mass of the substrate, the effects for swelling the substrate, dissociating lignin from the substrate and separating the hemicellulose having the molecular weight of the above range may not be expected to provide more effects than those. In addition, when the ammonia water exceeds 4 parts by mass with respect to 1 part by mass of the substrate, the energy required for heating the substrate mixture may become enormous.

In the process for producing a pretreated product for saccharification of the present invention, it is preferable to maintain the above substrate mixture at a temperature ranging from 25 to 100° C. for a period of time ranging from 1 to 100 hours.

When the temperature of the substrate mixture is below 25° C., the mixture may have to be maintained for a period of time exceeding 100 hours at the above temperature to swell the substrate, dissociate lignin from the substrate and separate the hemicellulose having the molecular weight of the above range. As a result, the energy required for heating the substrate mixture may become enormous.

On the other hand, when the temperature of the substrate exceeds 100° C., the time taken to maintain the mixture at the above temperature to swell the substrate and dissociate lignin from the substrate becomes less than 1 hour, hence making it difficult to manage the maintenance time. When the temperature of the substrate exceeds 100° C., the substrate contained in the substrate mixture is partially burned with each other or scorched and stuck to a reactor when maintained for a period of time longer than suitable.

DETAILED DESCRIPTION OF THE PREFERRED EMBODIMENTS

Hereinafter, the embodiment of the present invention is further described in detail with reference to the drawings attached herewith.

The pretreated product for saccharification of the present embodiment has rice straw as the lignocellulosic biomass substrate and is obtained by maintaining a substrate mixture obtained by mixing the substrate and ammonia water at a predetermined temperature for a predetermined period of time.

Figure 1:
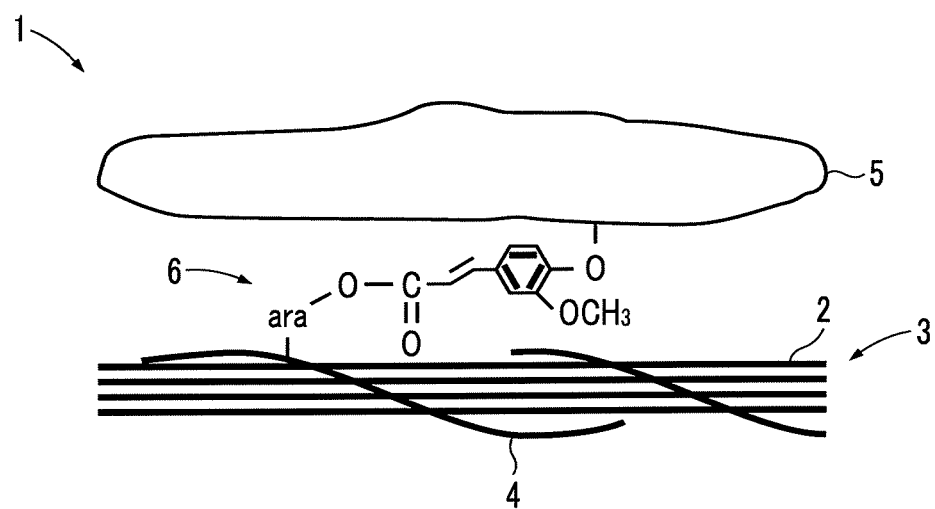
FIG. 1 is a schematic view illustrating the structure of rice straw.

As schematically shown in FIG. 1, rice straw 1 has a structure wherein hemicellulose 4 is positioned on the outer surface of microfibril 3 composed of cellulose 2 and further lignin 5 is positioned on the outer surface of the hemicellulose 4. The hemicellulose 4 is bonded to the lignin 5 via ferulate crosslinking 6. In the figure, —ara— refers to arabinose. Due to the structure the rice straw 1 has, when a saccharification enzyme is directly caused to act, the saccharification enzyme is blocked by the lignin 5 and hardly contacts the cellulose 2 or the hemicellulose 4, thereby failing to achieve efficient saccharification.

For this reason, in the pretreated product for saccharification of the present embodiment, 60 to 80% of all pores of the rice straw 1 have a diameter ranging from 10 to 50 nm. According to the pretreated product for saccharification of the present embodiment, owing to the above structure, the saccharification enzyme is readily absorbed into the rice straw 1, thereby improving the enzymatic saccharification efficiency. In addition, according to the pretreated product for saccharification of the present embodiment, owing to the above structure, the saccharified solution having a uniform quality can be obtained regardless of the quality difference in the rice straw 1 as the lignocellulosic biomass.

The pretreated product for saccharification can be produced as follows.

The rice straw 1 is first mixed with ammonia water in a concentration ranging from 20 to 30% by mass to prepare a substrate mixture. The substrate mixture, having the rice straw 1 as the substrate, is adjusted to have a mass ratio of the substrate:ammonia water=1:0.7 to 1:4.

The substrate mixture is then put into, for example, a reactor and maintained at a temperature ranging from 25 to 100° C. for a period of time ranging from 1 to 100 hours. In this way, the rice straw 1 swells by the action of the ammonia water, while the ferulate crosslinking 6 is cleaved, dissociating the lignin 5 from the rice straw 1. At the same time, of the hemicellulose 4 composing the rice straw 1, at least a part of the hemicellulose 4 having the molecular weight ranging from $7.8 \times 10^3$ to $2.0 \times 10^6$, for example 15% or more, is separated from the rice straw 1.

When the hemicellulose 4 having the molecular weight of the above range is separated from the rice straw 1, pores having a diameter ranging from 10 to 50 nm are formed between the dissociated lignin 5 and the microfibril 3 composed of the cellulose 2. Additionally, the pores having the diameter of the above range are formed in a range from 60 to 80% of all rice straw 1 pores.

As a result, the pretreated product for saccharification of the present embodiment having the structure described earlier can be obtained.

An Example of the present invention is described below.

EXAMPLE

In the present Example, a naturally dried rice straw was crushed using a cutter mill and those passed through a screen filter having a diameter of 3 mm were mixed with 25%-by-mass ammonia water in a mass ratio of the rice straw:ammonia water=1:4 to prepare a substrate mixture. The substrate mixture was then put into a reactor and maintained at 80° C. for 8 hours for the pretreatment to obtain a pretreated product for saccharification.

Subsequently, the obtained pretreated product for saccharification is suspended in a 50 mmol/L acetate buffer solution (pH 4) so as to be 10% by mass and maintained at 45° C. for 24 hours, and then the supernatant was collected. Sulfuric acid having the final concentration of 4% by mass was added to the supernatant, which was maintained in an autoclave at 121° C. for 1 hour. Subsequently, a sample wherein the sulfuric acid was added to the supernatant and a sample with no sulfuric acid added were measured for the concentration of monosaccharide of each of the samples by high performance liquid chromatography.

As a result, no monosaccharide was detected from the sample to which the sulfuric acid was not added, whereas monosaccharides such as glucose, xylose and arabinose were detected from the sample to which the sulfuric acid was added. Consequently, it is conceived that the supernatant contained a free sugar chain, and the monosaccharides described above were the hydrolysates of the sugar chain by the sulfuric acid. The sugar chain is also considered to have been derived from hemicellulose based on the structures of the monosaccharides.

The saccharide content in the rice straw was measured in conformity with the experimental protocol (see www.nrel.gov/biomass/pdfs/42618.pdf) recommended by NREL (National Renewable Energy Laboratory) and compared with the amounts of monosaccharides detected from the samples after treated in the autoclave as described earlier. The results revealed that the pretreated product for saccharification obtained in the present Example contained free hemicellulose, which accounts for 22% by mass of the entire hemicellulose contained in the rice straw.

Subsequently, 20 μL of 1 mol/L sodium nitrate was added to 180 μL of the supernatant, which was filtered using a 0.22 μm filter to obtain the hemicellulose. The molecular weight of the obtained hemicellulose was then measured by gel permeation chromatography (GPC). The result found that the molecular weight of the hemicellulose ranged from $7.8 \times 10^3$ to $2.0 \times 10^6$.

The rice straw contained in the pretreated product for saccharification obtained in the present Example was then deaerated at 100° C. under vacuum for 24 hours or more, and the pore size distribution of the rice straw was measured by the desorption technique using a fully automated gas sorption analyzer (a product of Quantachrome Instruments, tradename: Autosorp 1-MP-9). The result is shown in FIG. 2.

Figure 2:
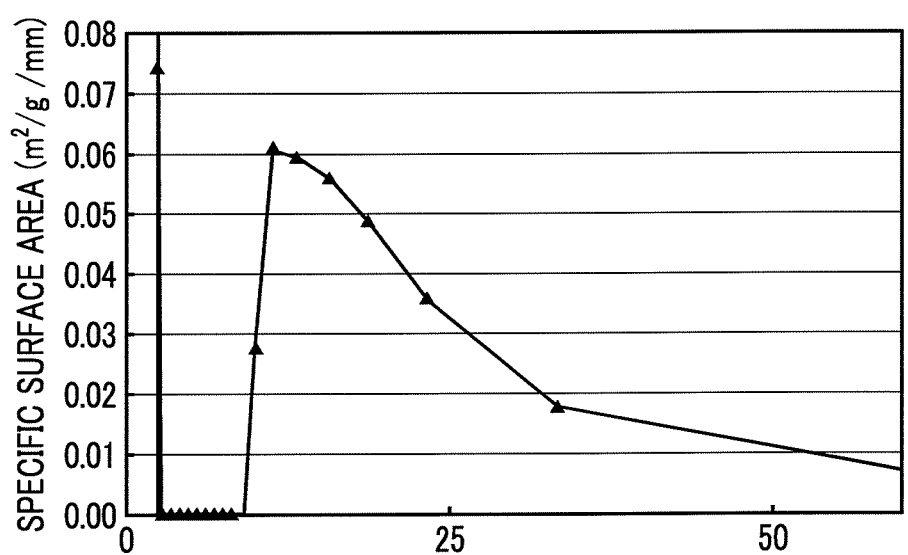
FIG. 2 is a graph showing the pore size distribution of rice straw contained in the pretreated product for saccharification of the present invention.

As shown in FIG. 2, the rice straw contained in the pretreated product for saccharification obtained in the present Example had 69% of all pores having a diameter ranging from 10 to 50 nm.

In addition, the rice straw contained in the pretreated product for saccharification obtained in the present Example and the rice straw not subjected to the above pretreatment (Comparative Example) used as the samples were deaerated at 100° C. under vacuum for 24 hours or more, and the relation between the pore size and the total pore specific surface area of each of the rice straws was measured by the desorption technique using the fully automated gas sorption analyzer (a product of Quantachrome Instruments, tradename: Autosorp 1-MP-9). The results are shown in FIG. 3.

Figure 3:
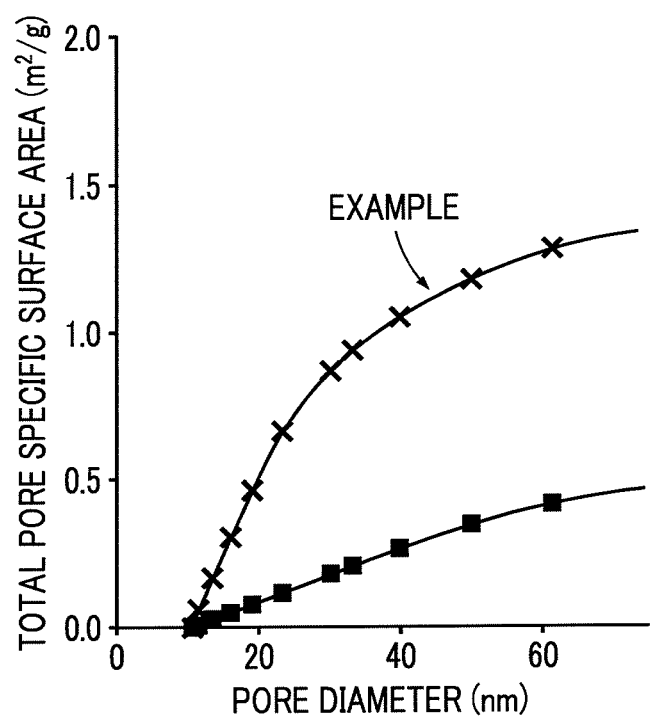
FIG. 3 is a graph showing, in comparison with a Comparative Example, the relation between the pore size and the total pore specific surface area of the rice straw contained in the pretreated product for saccharification of the present invention.

As shown in FIG. 3, the rice straw contained in the pretreated product for saccharification obtained in the present Example had the pores having a diameter of the above range in the range from 1.18 to 1.7 $m^2/g$, whereas the rice straw contained in the pretreated product for saccharification obtained in the Comparative Example had the pores having a diameter of the above range in the range below 0.3 $m^2/g$.

Subsequently, using as the samples the pretreated product for saccharification obtained in the present Example and the rice straw not subjected to the pretreatment (Comparative Example), a 50 mmol/L acetate buffer solution (pH 4) containing 0.5% by mass of the sample, 10% by mass of a saccharification enzyme (a product of Genencor, tradename: GC220) and 0.05% by mass of sodium azide was maintained at 50° C. for 3 days to carry out the enzymatic saccharification, whereby a saccharified solution was obtained.

The obtained saccharified solution was then centrifuged at 8000×g for 20 minutes and the obtained supernatant was heated at 95° C. for 5 minutes. The heat treated saccharified solution was subsequently centrifuged at 15000×g for 10 minutes, and the concentration of saccharide contained in the obtained supernatant was measured by high performance liquid chromatography.

Each of the centrifugal separation residues was dried at 105° C. for 24 hours, and the actual amount of the saccharide liquid was calculated by subtracting the dried mass from the mass of the saccharified solution. The saccharide content of the above rice straw was measured in conformity with the experimental protocol (see www.nrel.gov/biomass/pdfs/42618.pdf) recommended by NREL (National Renewable Energy Laboratory).

Thus, the saccharification ratio of each of the saccharified solution was calculated by the following formula. The results are shown in FIG. 4.

Saccharification ratio(%)=(concentration of saccharide×amount of saccharide liquid)/(amount of rice straw×saccharide content of rice straw)

Figure 4:
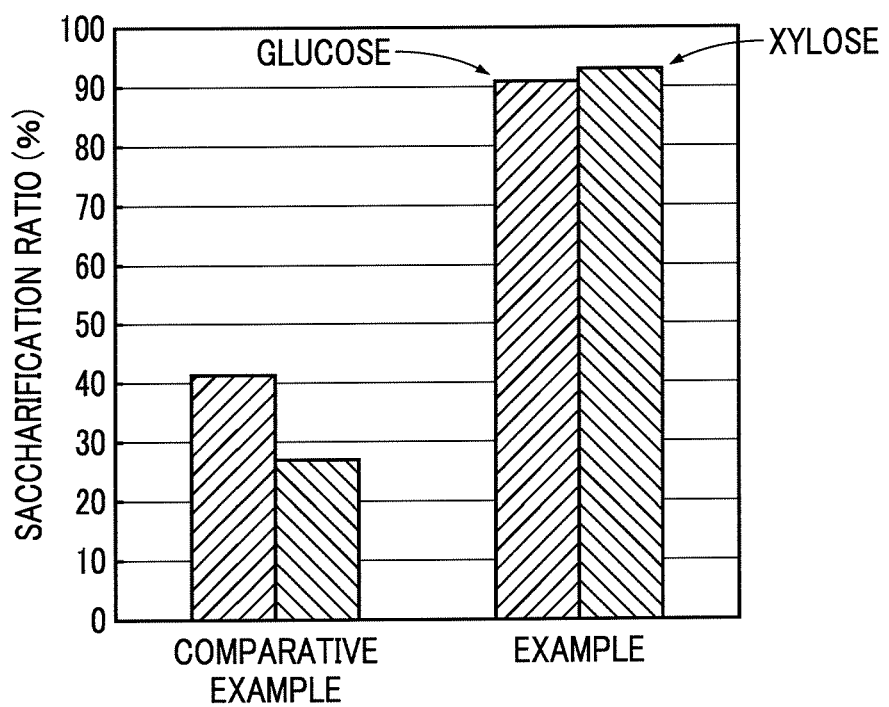
FIG. 4 is a graph showing, in comparison with the Comparative Example, the saccharification ratio of the saccharified solution obtained by enzymatically saccharifying the pretreated product for saccharification of the present invention.

FIG. 4 reveals that the pretreated product for saccharification of the present Example can achieve a much better saccharification ratio than the rice straw of the Comparative Example and the enzymatic saccharification can be efficiently carried out by the pretreatment alone.

What is claimed is:

1. A process for producing a pretreated product of lignocellulosic biomass for saccharification, in which lignin is dissociated from a substrate or the substrate is swelled, obtained by pretreating the lignocellulosic biomass as a substrate before saccharification, the process comprising:

maintaining a substrate mixture, obtained by mixing the substrate and ammonia water, at a predetermined temperature for a predetermined period of time to thereby separate at least 15% of hemicellulose having a molecular weight ranging from $7.8 \times 10^3$ to $2.0 \times 10^6$ of all hemicellulose included in the substrate; and forming pores between disassociated lignin and microfibril in the substrate, 60 to 80% of the pores having a diameter ranging from 10 to 50 nm, wherein the substrate mixture is obtained by mixing the substrate and ammonia water in a concentration ranging from 20 to 30% by mass in a mass ratio of the substrate: ammonia water=1:0.7 to 1:4.

2. The process for producing a pretreated product of lignocellulosic biomass for saccharification according to claim 1, wherein the substrate mixture is maintained at a temperature ranging from 25 to 100° C. for a period of time ranging from 1 to 100 hours.

3. A process for producing a pretreated product of lignocellulosic biomass for saccharification, in which lignin is dissociated from a substrate or the substrate is swelled, obtained by pretreating the lignocellulosic biomass as a substrate before saccharification, the process comprising:

maintaining a substrate mixture, obtained by mixing the substrate and ammonia water, at a predetermined temperature for a predetermined period of time to thereby separate at least 15% of hemicellulose having a molecular weight ranging from $7.8 \times 10^3$ to $2.0 \times 10^6$ of all hemicellulose included in the substrate; and forming pores between disassociated lignin and microfibril in the substrate, 60 to 80% of the pores having a diameter ranging from 10 to 50 nm, wherein the pores are formed such that a total pore surface area of the pores having a diameter in the range is between 1.18 and 1.7 $m^2/g$.

* * * * *